(12) United States Patent
Lisowsky et al.

(10) Patent No.: US 9,980,482 B2
(45) Date of Patent: May 29, 2018

(54) SYNERGISTIC COMPOSITIONS WITH PLANT PROTECTION AGENTS

(71) Applicant: multiBIND biotec GmbH, Cologne (DE)

(72) Inventors: Thomas Lisowsky, Monheim (DE); Karlheinz Esser, Moenchengladbach (DE)

(73) Assignee: multiBIND biotec GmbH, Koeln (DE)

( * ) Notice: Subject to any disclaimer, the term of this patent is extended or adjusted under 35 U.S.C. 154(b) by 49 days.

(21) Appl. No.: 15/030,635

(22) PCT Filed: Sep. 18, 2014

(86) PCT No.: PCT/EP2014/069921
§ 371 (c)(1),
(2) Date: Apr. 20, 2016

(87) PCT Pub. No.: WO2015/058910
PCT Pub. Date: Apr. 30, 2015

(65) Prior Publication Data
US 2016/0270391 A1 Sep. 22, 2016

(30) Foreign Application Priority Data

Oct. 22, 2013 (EP) .................... 13189755

(51) Int. Cl.
| | | |
|---|---|---|
| A01N 25/22 | (2006.01) | |
| A01N 47/12 | (2006.01) | |
| A01N 43/653 | (2006.01) | |
| A01N 59/20 | (2006.01) | |
| A01N 55/02 | (2006.01) | |
| A01N 37/34 | (2006.01) | |
| A01N 43/54 | (2006.01) | |
| A01N 25/24 | (2006.01) | |
| A01N 47/34 | (2006.01) | |
| A01N 37/36 | (2006.01) | |
| A01N 47/14 | (2006.01) | |
| A01N 59/16 | (2006.01) | |

(52) U.S. Cl.
CPC ............ *A01N 25/22* (2013.01); *A01N 25/24* (2013.01); *A01N 37/34* (2013.01); *A01N 37/36* (2013.01); *A01N 43/54* (2013.01); *A01N 43/653* (2013.01); *A01N 47/12* (2013.01); *A01N 47/14* (2013.01); *A01N 47/34* (2013.01); *A01N 55/02* (2013.01); *A01N 59/16* (2013.01); *A01N 59/20* (2013.01)

(58) Field of Classification Search
None
See application file for complete search history.

(56) References Cited

U.S. PATENT DOCUMENTS

2009/0186096 A1 7/2009 Kritzman

FOREIGN PATENT DOCUMENTS

| BR | PI0602068 A2 | 1/2008 |
|---|---|---|
| FR | 2917947 A1 | 1/2009 |
| WO | 2008144015 A2 | 11/2008 |
| WO | 2011140309 A2 | 11/2011 |
| WO | 2013068961 A1 | 5/2013 |

*Primary Examiner* — Kamal Saeed
(74) *Attorney, Agent, or Firm* — Agris & Von Natzmer, LLP; Joyce Von Natzmer

(57) ABSTRACT

The present invention relates to new, highly efficient synergistic compositions comprising mixtures of essential oils, metal ions, detergents and organic acids in combination with plant protection agents. That is, applied as an adjuvans or additive, said mixtures significantly increase the efficacy and biocompatibility of conventional plant protection agents for plant protection products. The new synergistic composition thereby allows significant reduction of active ingredients of conventional plant protection agents.

13 Claims, 6 Drawing Sheets

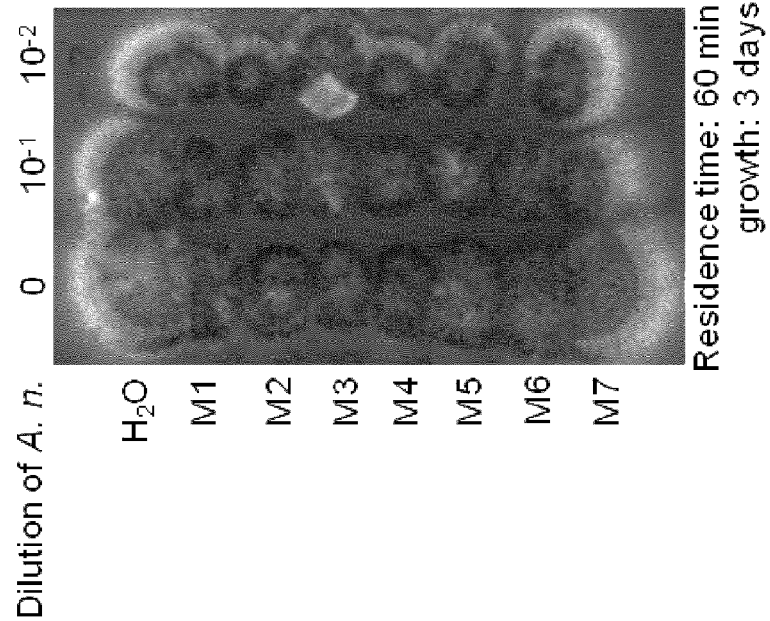
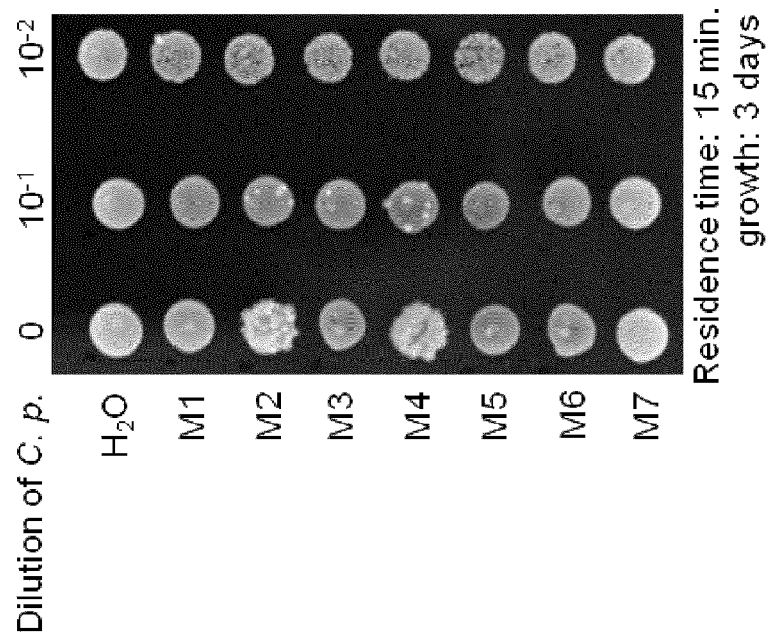

SYNERGISTIC COMPOSITIONS WITH PLANT PROTECTION AGENTS

CROSS-REFERENCE TO RELATED APPLICATIONS

This is the U.S. national stage of International application PCT/EP2014/069921, filed Sep. 18, 2014 designating the United States and claiming priority to European application EP 13189755.5, filed Oct. 22, 2013.

BACKGROUND

The present invention relates to a plant protection composition comprising at least one plant protection agent and a mixture for enhancing at least one activity of the plant protection agent. In particular, according to the invention highly efficient synergistic mixtures that, applied as an adjuvans or additive, are used to significantly increase the efficacy and biocompatibility of conventional plant protection agents for plant protection products. The synergistic mixture thereby allows significant reduction of active ingredients of conventional plant protection products.

PRIOR ART

Microbial contaminations in agricultural production cause severe problems and commercial losses. In general agricultural production world-wide is under the permanent pressure of infections by phytopathogenic viruses, bacteria and fungi. Therefore the use of plant protection agents is essential to secure yield and quality of agricultural products and to reduce economic losses. The constantly growing world population puts additional pressure on yield and quality of agricultural products as well as on the generation and synthesis of new plant protection agents. A major concern is also the biocompatibility of such plant protection agents and their impact on human health and the environment. In addition existing classical plant protection agents are reduced or even completely blocked in their efficacy by the appearance of resistances developed by adaptations of viruses, bacteria and fungi.

Besides the synthesis and generation of completely new plant protection agents the enhancement of the efficacy of established plant protection products is a suitable alternative.

Conventional plant protection agents used in well-established plant protection products with a broad spectrum against especially fungi are for example Propamocarb, Prothioconazole, Curzate, Mancozeb, Chlorothalonil, Azoxystrobin and Copperoxychlorid.

The listed conventional plant protection products are among the major plant protection products used world-wide against phytopathogenic fungi. The large quantities and the long time of usage of such conventional products bear environmental risks as well as risks concerning the development of resistances. Therefore the search for synergistic substances that increase the efficacy of conventional plant protection agents as well as the biocompatibility is a major demand and still unsolved problem of current agriculture. A higher efficacy would allow the substantial reduction of the amount of conventional plant protection agents necessary as active ingredients per hectare.

SUMMARY OF THE INVENTION

It is the object of the invention to overcome the current limitations and disadvantages of the prior art, to provide mixtures that significantly increase the efficacy and biocompatibility of conventional plant protection agents, and to develop plant protection compositions with reduced amount of plant protection agents.

The object is met by a plant protection composition comprising at least one plant protection agent and a mixture for enhancing at least one activity of the plant protection agent, wherein said mixture comprises:
a) at least one essential oil,
b) at least one type of organic acid,
c) at least one metal ion, and
d) at least one detergent.

Surprisingly, it was found that plant protection compositions comprising a conventional plant protection agent and a mixture comprising essential oils, organic acids, detergents and metal ions exhibit significant higher antimicrobial activities than the substances alone or incomplete mixtures of them. Accordingly, mixtures comprising essential oils, organic acids, detergents and metal ions, such as those described in EP 2 481 288 A1, surprisingly enhance the activity, i.e. efficacy, of conventional plant protection agents. Moreover, as said mixtures are highly biocompatible and the amount of plant protection agent in the composition can be significantly reduced, biocompatibility of the plant protection composition according to the invention is enhanced as well. Thus, one aspect of the invention is the use of a mixture comprising at least one essential oil, at least one type of organic acid, at least one metal ion, and at least one detergent for enhancing at least one activity of at least one plant protection agent.

Combining conventional plant protection agents with such mixtures enhances the general anti-microbial activity in a way that allows formulations with much lower concentrations of active ingredients from conventional plant protection agents but that are still as effective as the much higher concentrations of the active ingredients in conventional formulations. Lower concentrations of active ingredients also have many other positive effects concerning for example biocompatibility, toxicity, technical applications and commercial aspects.

Accordingly, the invention concerns new synergistic formulations to generate new plant protection products containing conventional plant protection agents for the treatment of all kind of phytopathogenic microorganisms.

The plant protection agent is, for example, selected from the group consisting of Propamocarb, Prothioconazole, Curzate, Mancozeb, Chlorothalonil, Azoxystrobin, and Copperoxychlorid.

Advantageously, it is sufficient that the plant protection agent is included in the plant protection composition according to the invention in concentrations that are about 50% to 80% lower in concentrations than in the conventional product. Depending on the specific conventional plant protection product the preferred lower concentration of the active ingredients are in the range from 0.001% to 0.1% (weight), in particular 0.05% to 0.01%, in relation to the total weight of the formulation. Accordingly, lower amounts of plant protection agents in the synergistic composition according to the invention are sufficient to still achieve a significant antimicrobial effect.

In one exemplary embodiment, the essential oil is included in concentrations from 0.005% to 0.5% (weight), in particular 0.01% to 0.05% (weight), in relation to the total weight of the composition.

The present invention generally relates to formulations with essential oils that are possibly but not exclusively selected from the following plant species as illustrating examples: tea tree (*Melaleuca alternifolia*) oil, Lavender (*Lavandula angustifolia*) oil, pine (*Pinus silvestris*) oil, manuka (*Leptospermum scoparium*) oil, kanuca (*Kunzea ericoides*) oil, eucalyptus (*Eucalyptus globulus*) oil, bergamot (*Citrus bergamia*) oil, clove (*Eugenia caryaphylata*) oil, lemon (*Citrus limoneum*) oil, lemon grass (*Cymbpogon citrates*) oil, rosemary (*Rosmarinus officialis*) oil, geranium (*Pelargonium graveoleus*) oil, Nimtree (*Azadirachta indica*) oil, mint oil or any other composition containing menthol and/or menthene or any mixture thereof.

The metal ion can be selected, for example, from the 4th group or sub-groups I, II, or VIII of the periodic table of the elements.

The metal ion may be included, for example, in concentrations from 0.0005% to 0.05% (weight), in particular 0.005% to 0.01% (weight), in relation to the total weight of the composition.

The invention-related applied metal ions can be, for example, di- and/or tri-valent ions of metals found in the 4th group and/or sub-group I, II and VIII of the periodic table of the elements, for example, one or several compounds selected from sub-group VIII, especially iron, cobalt, nickel, copper or zinc. They can be used as salts in combination with their organic and/or inorganic acids and bases.

The detergent may be included in concentrations from 0.005% to 0.05% (weight), in particular 0.01% to 0.05% (weight), in relation to the total weight of the composition.

The efficacy and biocompatibility of the plant protection composition according to the invention can be most notably increased if the plant protection agent and the detergent are included at a molar ratio of approximately 3:1.

The detergent may be at least one compound selected from the group consisting of anionic, amphoteric or cationic tensides, and suitable mixtures thereof.

The inventively applied detergents (i.e. surface-active substances) may be anionic, amphoteric or cationic tensides or suitable mixtures thereof. Especially, alkylethersulfate, alkyl- and/or arylsulfonate, alkylsulfate, amphotensides, betaines, alkylamidoalkylamines, alkyl substituted amino acids, alkyl substituted imino acids, acylated amino acids, and amphotenside combinations can be used. In principle all tensides supporting a positive synergistic effect are suitable.

In one exemplary embodiment, the organic acid can be included in concentrations from 0.005% to 0.5% (weight), in particular 0.01% to 0.05% (weight), in relation to the total volume of the composition.

The organic acids that may be used in preparing plant protection compositions of the present invention are either solid or liquid in their natural state and are readily soluble or dissolved in or miscible with water or an aqueous based solvent. Exemplary acids include the organic acids, especially the carboxylic acids such as citric acid, valeric acid, itaconic acid, acetic, citriconic acid, lactic acid, malic acid, succinic acid, aldaric acid, malonic acid, proprionic acid, malonic acid, maleic acid, salicylic acid, glutaric acid, tartaric acids, benzoic acid and the like.

For example, the plant protection composition according to the invention comprising conventional plant protection agents, essential oils, metal ions, detergents (surface-active substances) and organic acids for effective antimicrobial action according to the invention may include:
plant protection agent: 0.05%-0.01%
detergent: 0.05%-0.01%
organic acid: 0.05%-0.01%
essential oils: 0.05% to 0.01%
di- or tri-valent metal ions: 0.01% to 0.005%.

In order to further enhance the activity of the plant protection composition according to the invention, the molar ratio of conventional plant protection agents and detergents can be adjusted to about 3:1.

The plant protection composition according to the invention may further comprise, for example, additives, adjuvants, sticking or wetting agents and/or buffer substances, especially in order to render the composition suitable for specific applications.

Accordingly, the invention-related formulation may comprise additional common conventional adjuvans and additives like, for example, suitable sticking and wetting agents or buffer substances for defining a specific pH value.

If necessary, the pH value of the formulations according to the invention can be adjusted to a pH between 2 and 5 by the addition of suitable acids or buffer systems.

The ready-to-use plant protection product composition according to the invention can be used for all aspects of agricultural plant protection.

The plant protection composition according to the invention can be provided, for example, as a 100× fold to 10,000× fold concentrate. For example, concentrated formulations of 100× fold to 10,000× fold may be used for production and shipment.

In general, plant protection is achieved by spraying the composition according to the invention onto plants. The applied methods are however variable and can be adjusted to the different tasks.

According to one aspect of the invention, a method for treatment of a surface of a plant comprises the following steps: applying a composition to the surface, wherein said composition comprises at least one plant protection agent, at least one type of essential oil, at least one detergent, at least one metal ion, and at least one organic acid.

The object is also met by the use of a synergistic composition comprising at least one essential oil, at least one type of organic acid, at least one metal ion, and at least one detergent for enhancing at least one activity of at least one plant protection agent. According to the invention, a composition or mixture as described herein is provided, which significantly enhances at least one activity of at least one plant protection agent so that efficacy and biocompatible of a plant protection agent comprising said plant protection agent and said mixture can be significantly increased.

According to one aspect of the invention, a method for producing a plant protection composition is provided, wherein a mixture is added to at least one plant protection agent, said mixture comprising at least one type of essential oil, at least one detergent, at least one metal ion, and at least one organic acid.

In one embodiment of the aforementioned use or method, the plant protection agent can be selected, for example, from the group consisting of Propamocarb, Prothioconazole, Curzate, Mancozeb, Chlorothalonil, Azoxystrobin, and Copperoxychlorid.

In the following, the invention is exemplarily illustrated in detail with reference to the figures and tables.

BRIEF DESCRIPTION OF THE TABLES AND DRAWINGS

Table 1 shows selected conventional fungicides tested for synergistic activities and their abbreviations used in the figures and legends.

Table 2 shows selected mixtures (M1-M7) and concentrations of ingredients that are applied as additives or adjuvans in the listed tests for synergistic enhancement of the antimicrobial activities of conventional plant protection agents.

Table 3 shows the summary of synergistic effects determined in tests with *Candida parapsilosis* and spores of *Aspergillus niger* for mixtures with conventional plant protection agents.

FIG. 1A+B shows the control of mixtures (M1-M7) listed in table 2 for insufficient antimicrobial activities against A) *Candida parapsilosis* (C. p.) and B) spores of *Aspergillus niger* (A. n.).

DESCRIPTION OF EXEMPLARY AND PREFERRED EMBODIMENTS

A specific in vitro test system was designed with certified tester strains from *Candida parapsilosis* (DSM 70125) and spores from *Aspergillus niger* (DSM 1957) to define anti-microbial activities and synergistic effects. In all experiments freshly grown cultures of the listed microorganisms were adjusted to a cell number of about $10^5$ in a 200 µl volume of the test solutions. Test solutions are in general: a) sterile water ($H_2O$) as a negative control, b) conventional plant protection agent alone c) specific mixtures of essential oils, detergents, metal ions and organic acids, d) a plant protection composition according to the invention.

After a residence time of 15 min. (*Candida parapsilosis*) or 60 min. (*Aspergillus niger*) at room temperature the 200 µl samples containing the microorganisms and the test solutions were diluted and were plated in dilutions of 0, $10^{-1}$ and $10^{-2}$ with aliquots of 10 µl each onto growth media. After an incubation period of 2-5 days at 30° C. the grown colonies were determined and documented by digital photography.

In test samples with sterile water ($H_2O$), the conventional fungicides (F1-F7) or mixtures of essential oils, metal ions, detergent and organic acid (M1-M7) all microorganisms survived. Samples treated with the complete synergistic plant protection composition according to the invention did show substantial reduction of living cell colonies, indicating that under these conditions a higher antimicrobial efficacy was present. Thus it is proven that the different substances alone do not exhibit a special antimicrobial effect and also the mixtures of the components outside the scope of the invention are not effective or do only show a limited effect.

Surprisingly, the plant protection compositions according to the invention show significantly enhanced antimicrobial efficacies.

FIG. 1A+B shows the control of mixtures (M1-M7) listed in table 2 for insufficient antimicrobial activities against A) *Candida parapsilosis* (C. p.) and B) *Aspergillus niger* (A. n.). As it becomes apparent from FIG. 1A+B mixtures M1 to M7 with the specific ingredients and their specific concentrations do not have sufficient antimicrobial activities against *Candida* or *Aspergillus*.

Figure 2:
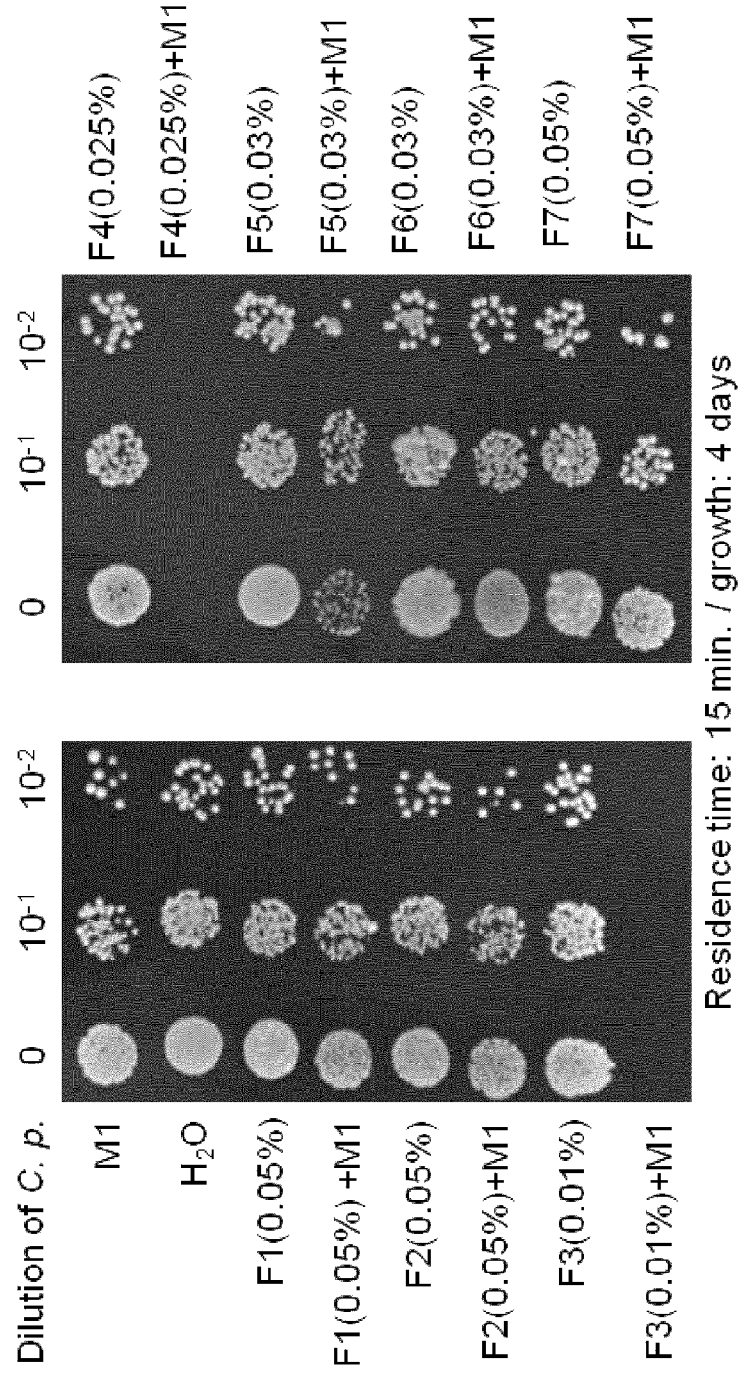
FIG. 2 shows the antimicrobial activities against *Candida parapsilosis* of conventional plant protection agents (listed in table 1) alone and the synergistic effect in combination with mixtures M1 (listed in table 2).

FIG. 2 shows the beneficial effect of different compositions according to exemplary embodiments of the invention on suspension cultures of *Candida parapsilosis*. Conventional plant protection agents F1 to F7 (listed in table 1) alone do not show sufficient antimicrobial activities against *Candida parapsilosis*. The combinations of plant protection agents F1 to F7 with mixtures M1 (listed in table 2) show synergistic effects. A digital image of the growth plate was taken after incubation. Spots showing no or only reduced growth of *Candida* colonies represent compositions having enhanced anti-microbial properties.

Figure 3:
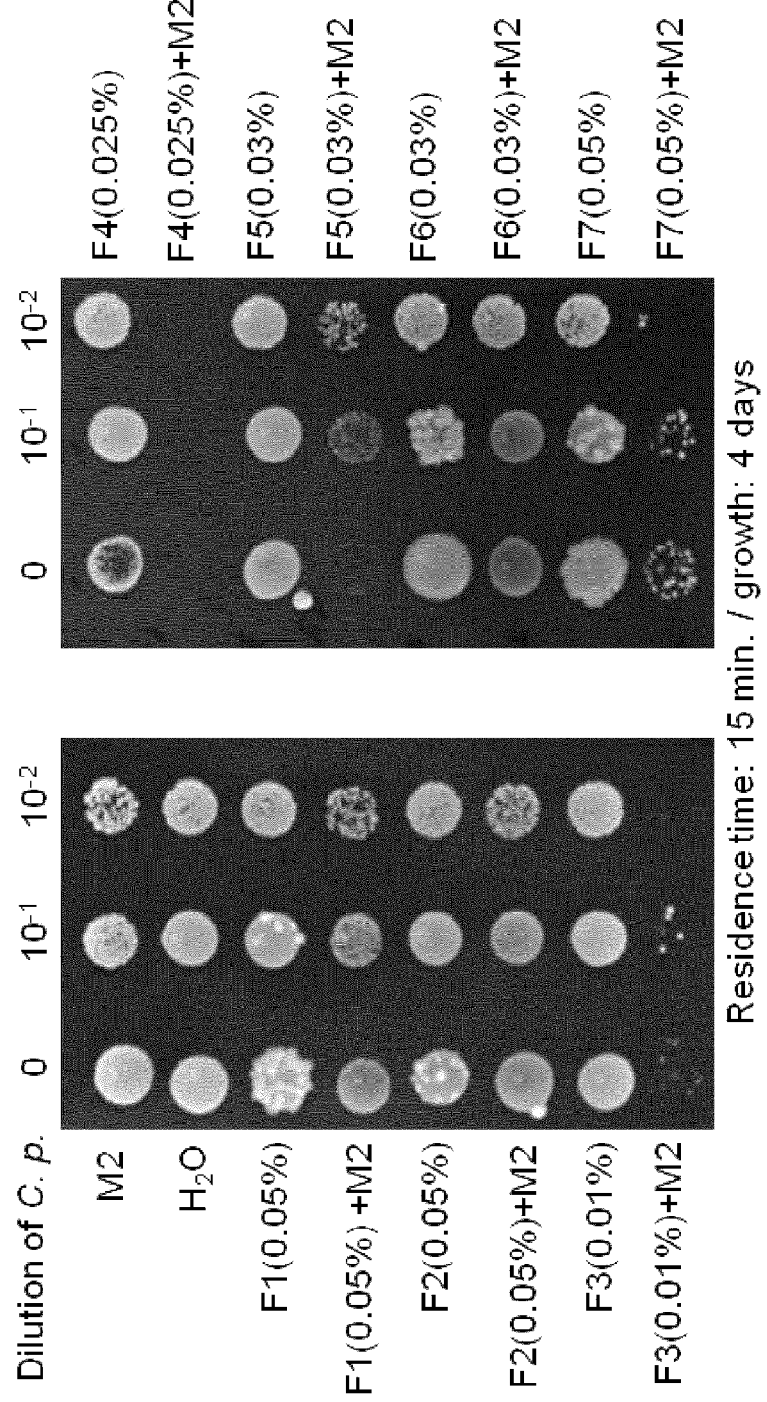
FIG. 3 shows the antimicrobial activities against *Candida parapsilosis* of conventional plant protection agents (listed in table 1) alone and the synergistic effect in combination with mixture M2 (listed in table 2).

FIG. 3 shows the beneficial effect of different compositions according to exemplary embodiments of the invention on suspension cultures of *Candida parapsilosis*. Conventional plant protection agents F1 to F7 (listed in table 1) alone do not show sufficient antimicrobial activities against *Candida parapsilosis*. The combinations of plant protection agents F1 to F7 with mixtures M2 (listed in table 2) show synergistic effects. A digital image of the growth plate was taken after incubation. Spots showing no or only reduced growth of *Candida* colonies represent compositions having enhanced anti-microbial properties.

Figure 4:
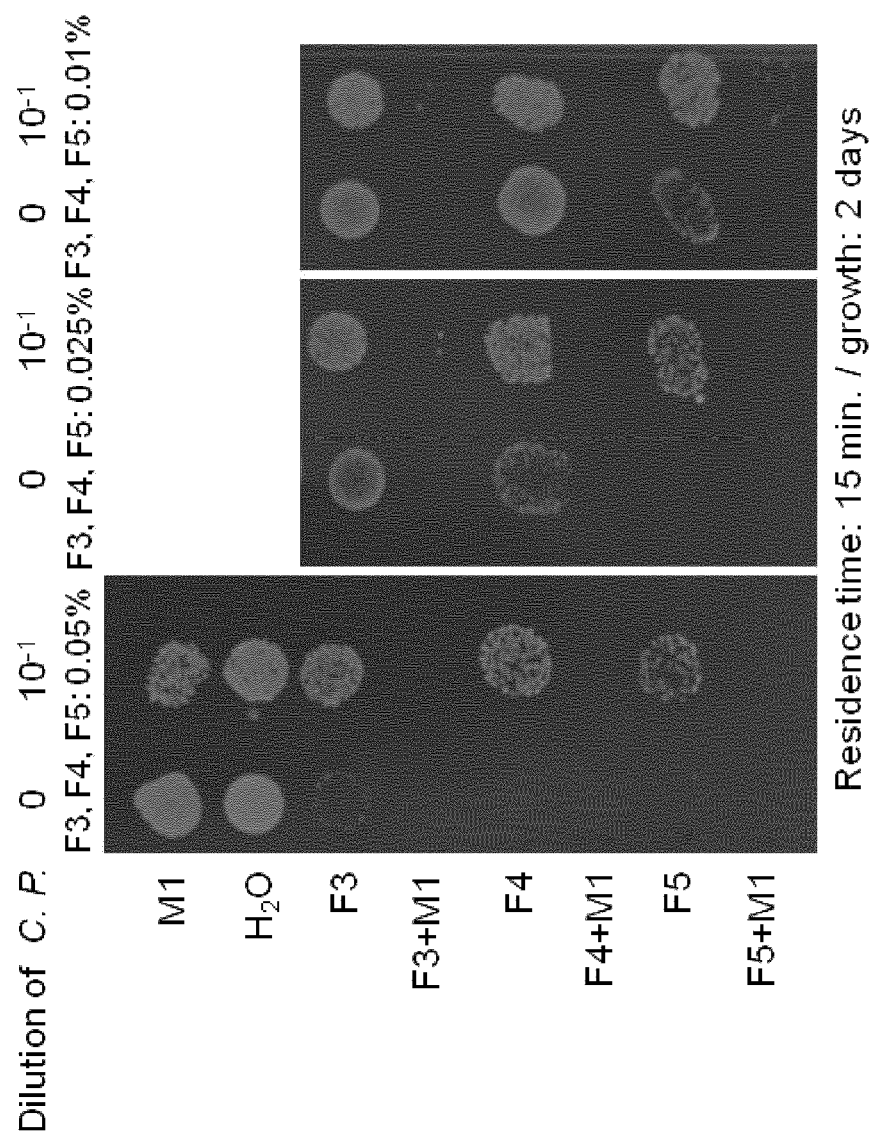
FIG. 4 shows antimicrobial activities against *Candida parapsilosis* of conventional plant protection agents F3-F5 (listed in table 1) at different concentrations and the synergistic effect in combinations with mixture M1 (listed in table 2).

FIG. 4 shows the beneficial effect of different compositions according to exemplary embodiments of the invention on suspension cultures of *Candida parapsilosis*. Conventional plant protection agents F3, F4 and F5 (listed in table 1) alone do not show sufficient antimicrobial activities against *Candida parapsilosis* at the listed three different concentrations (0.05%, 0.025%, 0.01%). The combinations of plant protection agents F3, F4 and F5 with mixtures M1 (listed in table 2) show synergistic effects for all three different concentrations. A digital image of the growth plate was taken after incubation. Spots showing no or only reduced growth of *Candida* colonies represent compositions having enhanced anti-microbial properties. As it becomes apparent from FIG. 4, the general efficiency of antimicrobial action of conventional plant protection products is enhanced by the addition of components of the synergistic mixtures, i.e. lower concentrations of conventional plant protection products are effective only with synergistic mixtures. With synergistic mixtures the amount of conventional plant protection agents can be substantially and advantageously reduced in the formulations. The magnitude of enhancement of activity is specific for each conventional plant protection agent.

Figure 5:
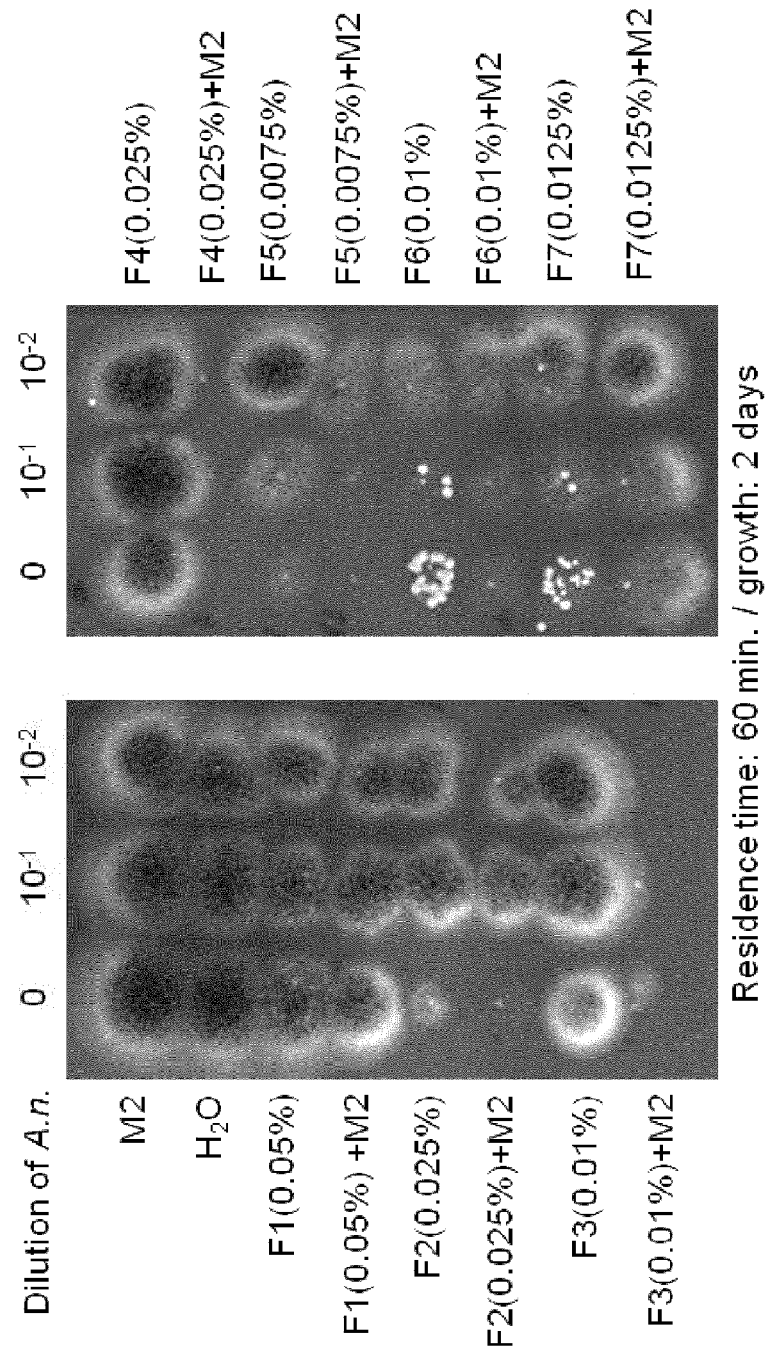
FIG. 5 shows anti-fungal activities against spores of *Aspergillus niger* of conventional plant protection agents (listed in table 1) alone and the synergistic effect in combination with mixture M2 (listed in table 2).

FIG. 5 shows the beneficial effect of different compositions according to exemplary embodiments of the invention on suspension cultures of spores from *Aspergillus niger*. Conventional plant protection agents F1 to F7 (listed in table 1) alone do not show sufficient antimicrobial activities against *Aspergillus* spores. The combinations of plant protection agents F1 to F7 with mixtures M2 (listed in table 2) show synergistic effects. A digital image of the growth plate was taken after incubation. Spots showing no or only reduced growth of *Aspergillus* myceles represent compositions having enhanced anti-microbial properties.

Figure 6:
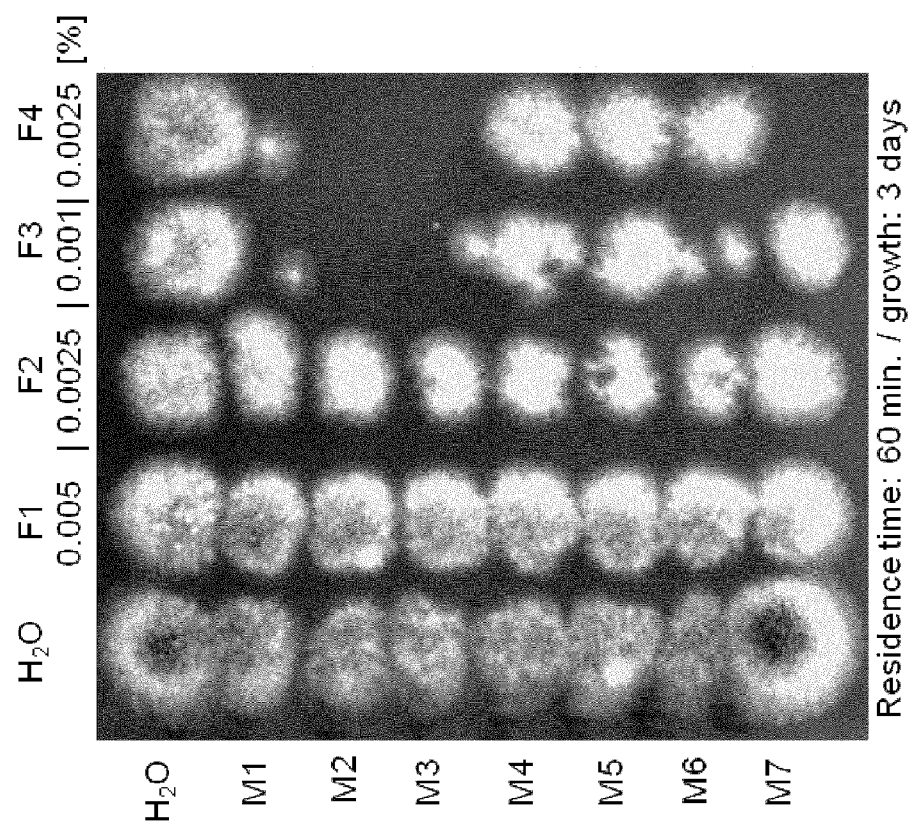
FIG. 6 shows anti-fungal activities against $10^3$ spores of *Aspergillus niger* in each sample of conventional plant protection agents F1 to F4 (listed in table 1) alone and the synergistic effect in combination with mixtures M1 to M7 (listed in table 2).

FIG. 6 shows the beneficial effect of different compositions according to exemplary embodiments of the invention on suspension cultures of spores from *Aspergillus niger* with concentrations of $10^3$ spores in each sample. Conventional plant protection agents F1 to F4 (listed in table 1) alone do not show sufficient antimicrobial activities against *Aspergillus* spores. The combinations of plant protection agents F1 to F4 with mixtures M1 to M7 (listed in table 2) show synergistic effects. A digital image of the growth plate was taken after incubation. Spots showing no or only reduced growth of *Aspergillus* myceles represent compositions having enhanced anti-microbial properties.

TABLE 1

Selected conventional fungicides tested for synergistic activities and their abbreviations (F1-F7) used in the figures and legends.

| | |
|---|---|
| F1 | Propamocarb |
| F2 | Prothioconazole |
| F3 | Curzate |
| F4 | Mancozeb |
| F5 | Chlorothalonil |
| F6 | Azoxystrobin |
| F7 | Copperoxychlorid |

TABLE 2

Table 2

| | M1 mg/L | M2 mg/L | M3 mg/L | M4 mg/L | M5 mg/L | M6 mg/L | M7 mg/L |
|---|---|---|---|---|---|---|---|
| Citric acid | 60 | 60 | | 100 | | 500 | |
| Lactic acid | 16 | 16 | | | 250 | | |
| Tartaric acid | | | 500 | | | | 250 |
| SOS (Sodium-Olefine-Sulfonate) | 160 | 160 | | | | | |
| SDS (Sodium-Lauryl-Sulfate) | | | 200 | | 200 | | 250 |
| SEHS (Sodium-2-EthylHexyl-Sulfate) | | | | 500 | | 500 | |
| Tea Tree Oil | 160 | | | | | 200 | |
| *Eucalyptus* Oil | | 160 | | 200 | | | 500 |
| Mint Oil | | | 200 | | 200 | | |
| $CuCl_2 \times 2H_2O$ | 40 | 40 | | | | | |
| $CuSO_4 \times 5H_2O$ | | | 40 | | | | 50 |
| $FeSO_4 \times 7H_2O$ | | | | | 100 | 5 | |
| $FeCl_3 \times 6H_2O$ | | | | | | 100 | |

TABLE 3

Table 3

| | concentration without sufficient antimicrobial activity | synergistic effect in mixtures |
|---|---|---|
| F1: Propamocarb | 0.05% | + |
| F2: Prothioconazole | 0.05% | + |
| F3: Curzate | 0.01% | +++ |
| F4: Mancozeb | 0.05% | +++ |
| F5: Chlorothalonil | 0.05% | ++ |
| F6: Azoxystrobin | 0.07% | + |
| F7: Copperoxychlorid | 0.05% | ++ |

Classification of synergistic effect:
+ = low but significant
++ = good
+++ = very good

The invention claimed is:

1. Plant protection composition comprising at least one plant protection agent in a concentration of 0.001% to 0.1% (weight) in relation to the total weight of the composition, wherein the plant protection agent is selected from the group consisting of Propamocarb, Prothioconazole, Cymoxanil, Mancozeb, Chlorothalonil, Azoxystrobin, and Copper oxychloride, and a mixture for enhancing at least one activity of the plant protection agent, wherein said mixture comprises:
   a) at least one essential oil in a concentration of 0.005% to 0.5% (weight) in relation to the total weight of the composition,
   b) at least one type of organic acid in a concentration of 0.005% to 0.5% (weight) in relation to the total volume of the composition,
   c) at least one metal ion in a concentration of 0.0005% to 0.05% (weight) in relation to the total weight of the composition, and
   d) at least one detergent in a concentration of 0.005% to 0.05% (weight) in relation to the total weight of the composition.

2. The plant protection composition according to claim 1, wherein the metal ion is from the $4^{th}$ group or sub-groups I, II, or VIII of the periodic table of the elements.

3. The plant protection composition according to claim 1, wherein the plant protection agent and the detergent are included at a molar ratio of about 3:1.

4. The plant protection composition according to claim 1, wherein the detergent is at least one compound selected from the group consisting of anionic tensides, amphoteric tensides, cationic tensides, and mixtures thereof.

5. The plant protection composition according to claim 1, further comprising additives, adjuvants, sticking or wetting agents and/or buffer substances.

6. The plant protection composition according to claim 1, wherein, for production and shipment, said composition is provided as a 100× fold to 10000× fold concentrate.

7. Method for treatment of a surface of a plant, said method comprising:
   applying the plant protection composition of claim 1 to the surface.

8. Method for enhancing at least one activity of at least one plant protection agent comprising adding at least one essential oil in a concentration of 0.005% to 0.5% (weight) in relation to the total weight of the composition, at least one type of organic acid in a concentration of 0.005% to 0.5% (weight) in relation to the total volume of the composition, at least one metal ion in a concentration of 0.0005% to 0.05% (weight) in relation to the total weight of the composition, and at least one detergent in a concentration of 0.005% to 0.05% (weight) in relation to the total weight of the composition to said at least one plant protection agent, wherein the at least one activity of said at least one plant protection agent is enhanced, and wherein said at least one plant protection agent is provided in a concentration of 0.001% to 0.1% (weight) in relation to the total weight of the composition and selected from the group consisting of Propamocarb, Prothioconazole, Cymoxanil, Mancozeb, Chlorothalonil, Azoxystrobin, and Copper oxychloride.

9. Method for producing a plant protection composition, adding the mixture of claim 1 to the at least one plant protection agent, wherein said at least one plant protection agent is provided in a concentration of 0.001% to 0.1% (weight) in relation to the total weight of the composition and wherein the plant protection agent is selected from the group consisting of Propamocarb, Prothioconazole, Cymoxanil, Mancozeb, Chlorothalonil, Azoxystrobin, and Copper oxychloride.

10. The plant protection composition according to claim 1, wherein the essential oil is included in concentrations from 0.01% to 0.05% (weight) in relation to the total weight of the composition.

11. The plant protection compositions according to claim 1, wherein the metal ion is included in concentrations from 0.005% to 0.01% (weight) in relation to the total weight of the composition.

12. The plant protection composition according to claim 1, wherein the detergent is included in concentrations from 0.01% to 0.05% (weight) in relation to the total weight of the composition.

13. The plant protection composition to claim 1, wherein the organic acid is included in concentrations from 0.01% to 0.05% (weight) in relation to the total volume of the composition.

* * * * *